United States Patent [19]

Jüng

[11] 3,966,493

[45] June 29, 1976

[54] RECHARGEABLE MERCURY ELECTRODE

[75] Inventor: Margarete Jüng, Kelkheim, Taunus, Germany

[73] Assignee: Varta Batterie Aktiengesellschaft, Hannover, Germany

[22] Filed: Dec. 6, 1972

[21] Appl. No.: 312,434

Related U.S. Application Data

[63] Continuation of Ser. No. 23,918, March 30, 1970, abandoned.

[30] Foreign Application Priority Data

Apr. 2, 1969 Germany............................ 1916959

[52] U.S. Cl.................................. 136/20; 136/68; 136/120 R
[51] Int. Cl.²...................................... H01M 35/02
[58] Field of Search .................. 136/20, 23, 24, 28, 136/25, 107, 86 D, 120 R, 120 FC, 137, 3, 7, 68, 100 R

[56] References Cited

UNITED STATES PATENTS

| | | |
|---|---|---|
| 2,536,699 | 1/1951 | Ruben................................ 136/107 |
| 2,677,006 | 4/1954 | Ameln................................. 136/20 |
| 2,901,523 | 8/1959 | Justi et al.......................... 136/86 D |
| 3,150,011 | 9/1964 | Winsel et al................... 136/120 FC |
| 3,236,690 | 2/1966 | Booe et al............................. 136/68 |
| 3,310,436 | 3/1967 | Ralston et al........................ 136/20 |
| 3,429,751 | 2/1969 | Heuse................................. 136/120 |
| 3,522,094 | 7/1970 | Richman.............................. 136/86 |
| 3,698,953 | 10/1972 | Eisenberg ............................ 136/20 |

FOREIGN PATENTS OR APPLICATIONS 1,224,380  9/1966  Germany............................. 136/20

Primary Examiner—Anthony Skapars
Attorney, Agent, or Firm—Weiser, Stapler & Spivak

[57] ABSTRACT

A rechargeable mercury/mercury oxide electrode having a high capacity, especially for primary cells and accumulators, which has a metal matrix with a non-pyrophoric amalgam. The electrode is capable of repeated charging and discharging cycles during which the mercury is present as mercury oxide and mercury, respectively. The electrode is capable of a flat and constant discharge curve, with an electrical current discharge approaching the theoretical capacity of the electrode.

17 Claims, 5 Drawing Figures

RECHARGEABLE MERCURY ELECTRODE

This application is a continuation of application Ser. No. 23,918 filed Mar. 30, 1970, and now abandoned.

This invention relates to a new alloy of Raney metal, an electrode thereof, a cell and battery using such electrode, and methods of making the electrodes.

For a long time mercuric oxide has been used as the active material, as the electrolytically reducible oxygen-yielding compound in primary cells. The first technically useful cell of this type has been described in U.S. Pat. Nos. 2,422,045 and 2,422,046 to Ruben. These cells are used as primary cells because a renewed charge of the metallic mercury which is formed during discharge is ineffective to recharge the cell. During discharge the mercury coalesces into droplets which at most can be coated on their surface with a thin oxide film during recharging of the cell.

German Patent Disclosure No. 1,160,909 discloses an alkaline accumulator which contains a mercuric oxide as electrochemical substance, which is described rechargeable. To ensure recharging the accumulator contains zinc at the counter electrodes as the electrochemically active material; the quantity of zinc is so adjusted that the zinc is already used up before the complete reduction of the mercury (II) + oxide; at the end of the discharge no mercury not only mercury (I) oxide is present. In order to keep the latter in a dispersed state, and to improve the electrical conductivity of the electrode, silver powder and graphite or activated coal is added to the active material.

It has been further proposed to mix mercury (II) + oxide with powdered silver in order to ensure the formation of finely divided silver amalgam during the discharge. It is evident from "Mercury Cell Battery Investigation," *Techn. Document Report* No. APL-TDR-64-15, U.S.A., Library of Congress, than an increasing separation into the two metals takes place with number of cycles; such separation then leading to increasing portion metallic mercury which is not rechargeable.

According to a more recent process, more fully described in German Patent Disclosure No. 1,224,380, it is proposed to use as active material mercury (II) oxide, coprecipitated with nickel hydroxide, washed and saturated, then mixed with graphite. A mixture consisting of 20% Ni (OH)$_2$, 70% HgO, and 10% micropulverized graphite is described as giving particularly good results. Cells equipped therewith stated to be rechargeable and to retain essentially their full capacity even after a great number of charge-and-discharge cycles when the negative zinc amalgam electrode contains 5 to 30 per cent by weight, especially, 20 per cent by weight of silver.

The problem existing prior to the invention was to find a mercury/mercuric oxide electrode which is not only rechargeable but also is inert to the material of the counter electrode and which does not coalesce to mercury pellets. It is also very desirable that the material be inexpensive and be manufaactured in a simple manner.

The instant invention provides such an electrode. Moreover, in the course of this work, a new alloy was unexpectedly discovered which is a Raney metal, like Raney nickel or Raney iron with mercury wherein the mercury content ranges preferably from 50 to 80 per cent by weight. The alloy is unique in its physical properties. It is a powder which though mobile is just so slightly sticky as not to have the fluidity and elusiveness of mercury; nor does the powder coalesce into droplets or globules or into separate phases of the mercury within the other metal as is conventional. The alloy is admirably suited as an electrode, as a reference electrode, for electrochemical reactions and also for various chemical reactions for instance as a catalyst in organic chemical reaction where selective oxidation or epoxidations are carried out.

An important advantage of the catalyst is that it be reoxidized and reused. Its physical characteristics permit it to be filtered out of the organic reactants. For instance, mercury and its salts and various amalgams are useful as catalysts in hydrogenations and dehydrogenations. See *Catalysis*, Berkman et al. Reinhold Pub. Corp. 1940, pages 367, for the catalytic hydrogenation of ketones, page 826, of oxygen containing compounds, page 839, in catalytic polymerizations for instance of olefins and acetylenic compounds and other monomers, this reference being incorporated herein by reference. The alloy of the invention is particularly well suited for use as an electrode. It lends itself to various electrochemical uses, as disclosed for instance in the *Encyclopedia of Electrochemistry*, Hampel, Reinhold Pub. Corp. 1964, page 403.

The invention provides, as one of its major embodiments, an electrode which overcomes to a very large extent the above mentioned problems. The electrode of the invention contains mercury oxide in the charge state and mercury when it is discharged, in a metal matrix which has a dissolving property for hydrogen.

Metals which have the capacity to dissolve hydrogen are known. See for instance Catalysis, above cited, Diffusion in Contact Catalysis at p. 106–122. The metals which are preferred at the present time are specific Raney metals: Raney nickel, Raney iron and Raney cobalt.

Figure 1:
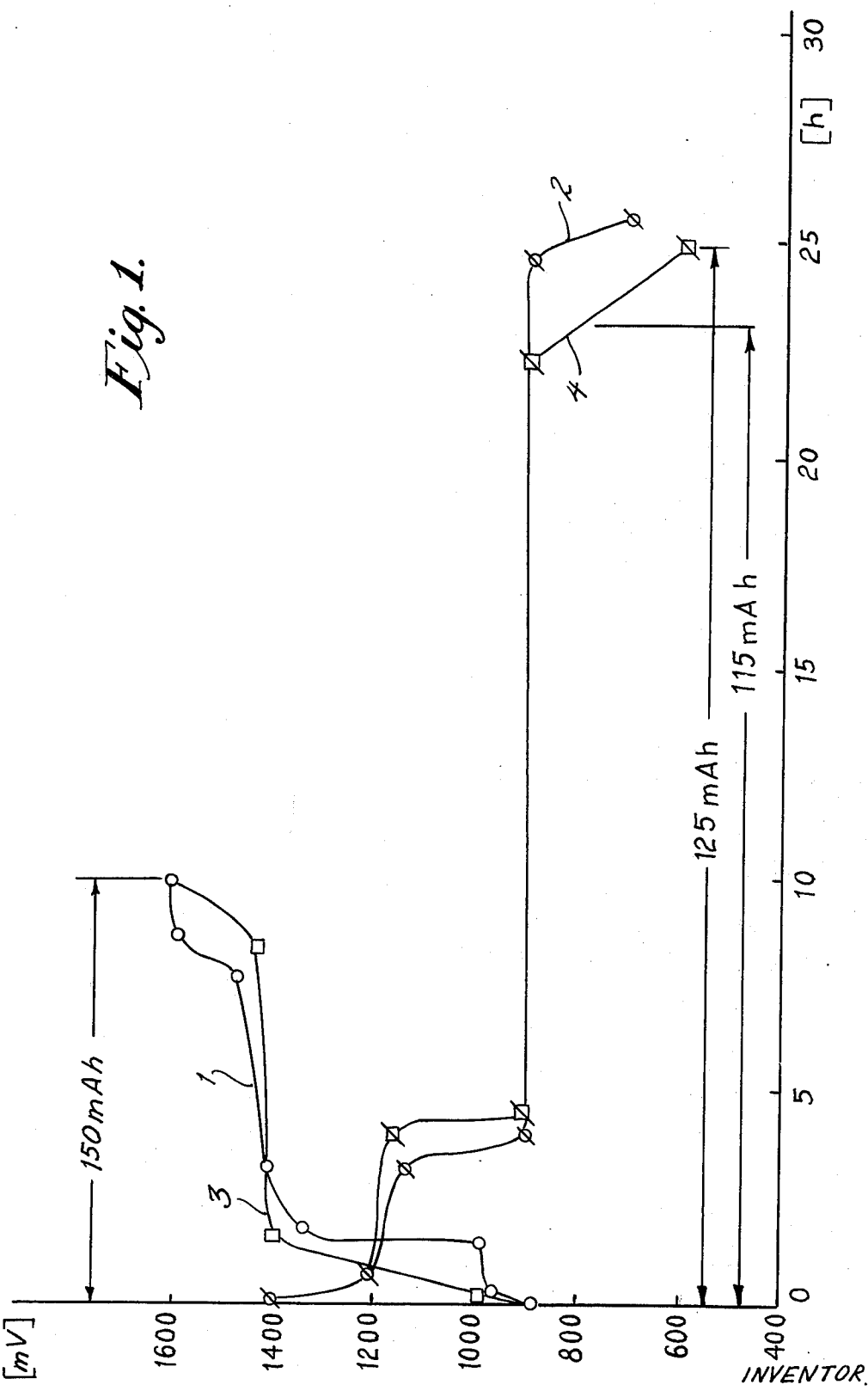
FIGS. 1 and 2 show typical charge and discharge curves of cells of the invention.

In accordance with the invention, the electrode is formed of the metal matrix with which the mercury forms the alloy.

The matrix, especially when highly porous, functions to prevent the mercury from flowing together to form droplets; the matrix is porous. The mercury remains in an extremely fine state of physical distribution over many electrical cycles and, therefore, remains rechargeable. Nickel, iron and cobalt, as well as alloys of these metals have proved to be highly suitable for the metal matrix. For example, nickel flakes and carbonyl-nickel powder can readily absorb up to 30 to 80 per cent by weight of mercury. Those of the named metals and quite especially metal alloys that evidence a Raney-structure have proved to be useful as matrices for the sorption of the mercury and mercury oxide. Of the alloys, nickel/iron and nickel/iron/cobalt have proved to be especially useful.

Likewise highly suitable are nickel powder, for example, carbonyl-nickel powder. Nickel flakes are highly desirable because of their good conductivity and physical scaly form. The flakes can be readily amalgamated. The electrode contains a higher content of mercury and at the discharge of the cell, the potential step NiOOH — Ni (OH)$_2$ is more effectively suppressed.

It is advantageous to increase the conductivity of the electronically reducible metal oxygen-yielding compound to admix to the active metal portion approximately 2 to 30 per cent by weight of graphite, acetylene black or other conductive known metal.

The manufacture of the electrode of the invention comprises charging the metal which is to form the matrix with hydrogen and then bringing it into close contact with a solution of a mercury salt to cause amalgamation, until the desired mercury amount is amalgamated onto the metal.

Subsequently, the amalgamated metal is separated from the treating solution like by washing and drying. The powder is formed into an electrode if desired. If desired another binding and/or conducting metal is added to the electrode body.

The charging of the metal matrix with hydrogen can be promoted by various procedures. In one embodiment hydrogen is introduced into the metal by means of a treatment with strongly reducing, hydrogen-yielding agents. Well suited for this purpose are aqueous solutions of complex hydrides, such as Mydrazine or alkali boranate solutions. Another embodiment is to treat the matrix material, i.e. the Raney alloys, especially, alloys of the metals nickel, iron, and cobalt, separately, or alloyed to each other, with acides, gases, water or other hydroxy-containing compounds to dissolve out the inactive metal component, as Al, Zn, Mg, Si, Ca, and Li. Preferably there is present in the solution a complex-forming chemical which will keep the dissolved component in solution. By this method, large amounts of hydrogen are built into the remaining metal.

It is advisable under certain circumstances to promote the incorporation of hydrogen to treat the matrix material (from which the inactive component has been dissolved) with aqueous solutions of complex hydrides. The treatment with the complex hydrides or alkali boranates can follow the treatment with the mercury salt, or precede it or be timed between two such treatments. It is highly desirable to conduct the charging with hydrogen (after removing the inactive component) at the lowest possible temperature since at these temperatures the sorbtion of larger amounts of hydrogen by the metal is promoted. Suitable low temperatures range from about 20° to 35° C. The incorporation of mercury is carried out preferably in an alkaline aqueous medium.

For the preparation of the amalgam of the Raney metal any salt of mercury is suitable, preferably a water-soluble mercuric (II) or mercurous (I) salt. Typical salts include mercurous nitrate, mercuric acetate, mercuric bromide mercuric chloride, mercurous chlorate and mercuric chlorate, mercuric sulfate, and the like.

With some of these salts, a portion of the dissolved hydrogen is consumed by the reduction of the ions to amonia, such as occurs with mercuric or mercurous nitrate. It is therefore advisable to use mercury salts or complexes which are free of reducible anions. Mercuric chloride $HgCl_2$ is ideally suited for this purpose.

The progress and completion of the amalgamation is detected by the alkaline solution taking on a yellowish coloration caused by the formation of HgO. After washing and drying of the powder obtained there can be added an electrically conducting material such as nickel flakes, carbonyl nickel, and graphite. If desired there is admixed, a binding material. In another preferred variant of the invention there can be added a pore forming material to the metal alloy. The particle size for such purpose can range from about 70 $\mu$ to 300 $\mu$ in diameter with equivalent satisfactory results.

In order to place the electrode into the charged state, it has been found to be practical to treat it electrochemically already prior to the insertion into the battery, so that the mercury be converted into mercuric oxide. This electrochemical treatment can, however, also be carried out when the electrode is already inserted into the cell. The mercury-containing electrode can be charged also purely chemically, namely, by the action of oxygen, if desired under increased pressure.

The electrode of the invention are not only useful in applictions where there repeated charges and discharges take place but also economical and useful even when only one discharge takes place, this in part due to the nature of the matrix.

This is particularly so for electrodes which are discharged very slowly over an extended time period. In conventional electrodes and cells, the mercury already formed migrates partially to the counter electrode and moreover covers the mercuric oxide still present on the mercuric oxide electrode. Hence in very slow discharging batteries, like clock or watch batteries it was only possible to draw approximately only one half of the theoretical capacity of current delivery, whereas in the present cells the current drawn approximates closely the theoretical capacity.

The invention is further illustrated by the following non-limitative examples.

EXAMPLE 1

1. There is introduced with thorough cooling and agitation 100 g Raney-nickel alloy (50 percent Ni, 50 per cent Al both by weight; grain size smaller than 40$\mu$) into 2 liter of 6 N NaOH in which 20 g potassium-sodium tartrate is dissolved (as a complex former for the $Al^{3+}$ -ion), so that the temperature of the alkali remain low. Under these conditions the Raney-nickel sorbes more hydrogen, and therewith later on more mercury. After approximately 2 to 3 hours strong hydrogen evolution subsides indicating completion of the reaction.

To amalgamate the Raney-nickel, 200 g of mercuric chloride, $HgCl_2$ is dissolved in 6 liter of water with addition of some hydrochloric acide to suppress hydrolysis. This solution is slowly added to the above prepared solution with active agitation. The completion of amalgamation is shown by a weak yellow coloration of the solution resulting from the formation of mercuric oxide. The finished sample is washed until it is free of alkali and cloride. Subsequently, the filter cake is washed with acetone and dried in air. The amalgamated Raney-nickel is a nonpyrophoric powder. It is a free flowing powder (not a liquid, like mercury) greenish in color.

The x-ray diagram of the freshly prepared amalgam clearly shows the characteristic peaks for $NiHg_4$; upon prolonged storage in air the $NiHg_4$ becomes amorphous.

There are mixed 10 g of the amalgamated powder with 2 g of graphite; 1.5 g of this mixture is filled in between two sieves and compressed under a pressure of 2000 kg/cm². A useful electrode is obtained.

2. In further experiments, graphite is omitted and 10 g of the amalgamated Raney-nickel is mixed with 2 g nickel flakes as an additional conducting material. The electrodes were made in accordance with the above described method from this mixture.

EXAMPLE 2

The electrodes are inserted into cells with cadmium electrodes. Each cadmium electrode exhibits approximately five times the capacity of the HgO-electrode. The capacity of the cells is thus determined by the lower capacity of the HgO-electrode. The cell is operated with 4.5 N KOH as electrolyte at room temperature (18°C to 22°C).

The measurements are carried out with an automatically operated charging and discharging device. The discharge is interrupted then when the HgO-electrode shows a polarization of 400 mV and the total voltage of the cell, therefore, has declined to 500 mV.

FIG. 1 shows a charge curve 1, and a discharge curve 2 for an electrode which contains graphite as conducting material; its Hg-content amounts to 47.18 per cent by weight (without the weight of the sieve). It was charged with 15 mA for 10 hours, discharged with 5mA. As is shown by curve 1, first the theoretical voltage of the Hg/HgO — Cd/Cd(OH)$_2$ -cell is reached by charging for 1.5 hours; then the voltage suddenly increases by 400 mV and remains at this value for approximately 6 hours before it increases again by 150 mV. During discharge, the electrode remains at the NiO(OH)/Ni(OH)$_2$ -potential for 4 hours (20 mAh), then the Hg/HgO -potential is established and remains constant over 21 hours at (105 mAh).

FIG. 1 also shows charge curve 3 and discharge curve 4 which have been obtained with an electrode that contains Ni-flakes as conducting material at practically the same Hg content (47.2 per cent by weight). The electrode was charged with 15mA and discharged with 5mA. During charging the electrode reaches the HgO-potential already in 0.5 hour. During discharge, it remains for 4.25 hours at the NiO(OH)/Ni(OH)$_2$ -potential (21.25 mAh) and then remains constant at the Hg/HgO potential for 19.5 hours (97.5 mAh).

Figure 2:
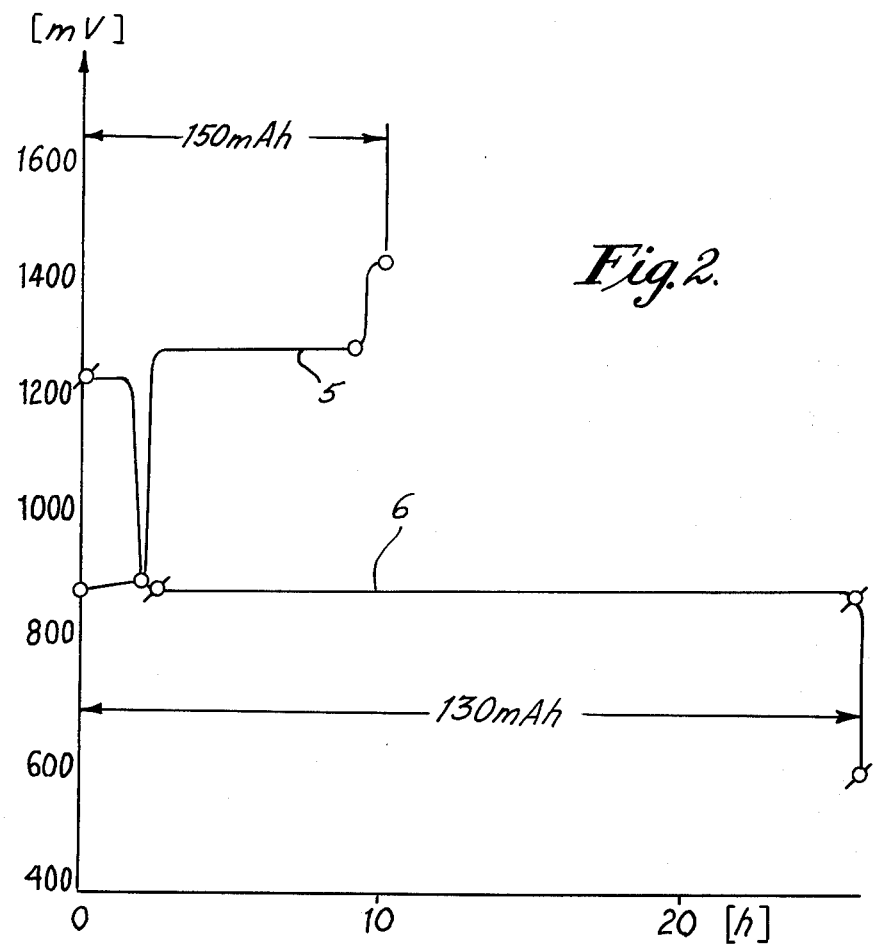

FIG. 2 shows charge curve 5, and discharge curve 6 of another electrode that contains graphite as conducting material. The amalgamated Raney-nickel has an Hg content of 60.48 per cent by weight. The third charge- and discharge-cycle is shown here. From the charge curve, it is apparent that the over voltage is smaller than with the electrodes, according to FIG. 1 (which have an Hg-content of 47.2 per cent by weight). During discharge of this electrode (with the higher Hg-content) it is established as shown by curve 6, that the electrode remains at the higher potential of the nickel oxide only for 2.5 hours, then remains constant at the Hg/HgO potential. The total capacity of this electrode remains at 130 mAh, the HgO-capacity is still at 117.5 mAh.

Figure 3:
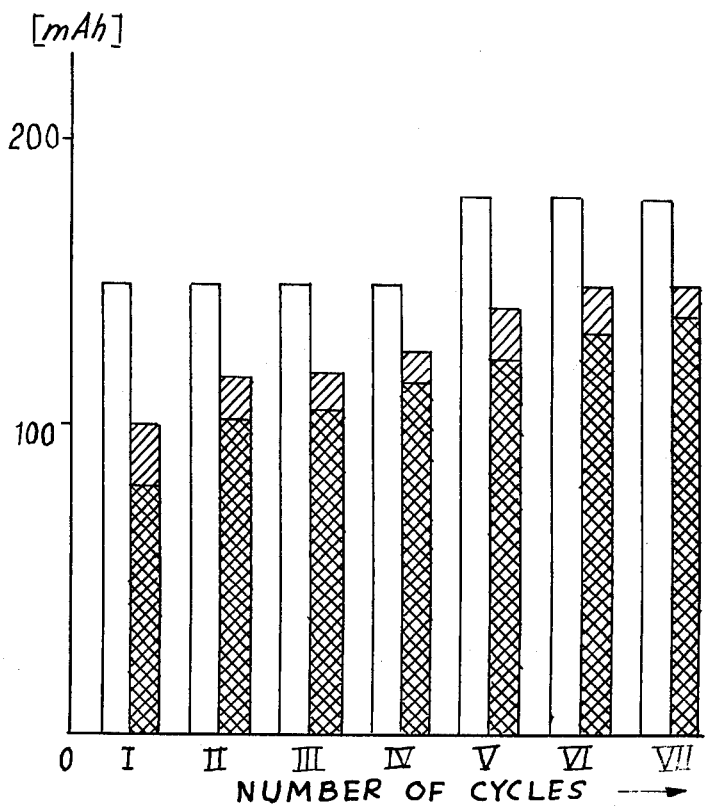
FIG. 3 show repeated charge and discharge cycles of the electrode of the invention.

FIG. 3 shows graphically the results of the first seven charge- and discharge cycles. The unshaded bar is a measure of the charged electrical energy (mAh); the shaded bar a measure of the total energy (mAh) to be discharged from the charged electrodes, the crisscrossed shaded part of the bar shows that portion attributable to the discharge of the HgO. During the first 4 cycles the same electrode which is shown in FIG. 2, is charged in the Cd-Hg cell for 10 hours with 15mA. The HgO-capacity rises from 82 mAh to 117 mAh. With the 5th to the 7th cycle the electrode is charged with 15 mA for 12 hours. Under these conditions, the portion of the electrode which can be discharged at the Hg0-potential increases and at the 7th discharge, amounts to 140 mAh.

Long term measurements show that the capacity of the electrode increases further slowly; at the 50th cycle, the discharge capacity of the HgO is still 145 mAh.

EXAMPLES 3 to 8

The amount of mercury which can be introduced as the alloy ingredient depends to a large extent on the activation conditions and on the grain size of the Raney-metal. This is shown below. In all cases a same Raney-nickel alloy (50% Ni and 50% Al both by weight) and an aqueous HgCl$_2$ -solution was used as the Hg-source. The following table shows the results.

| Ex. | Grain Size | Activation | % Hg | % Ni | % Al |
|---|---|---|---|---|---|
| 3 | >100 μ | Activation under cooling | 54.48 | 32.44 | 3.42 |
| 4 | <40 μ | Activation under cooling | 60.48 | 27.14 | 3.95 |
| 5 | 5 – 10 μ | Activation under cooling | 61.78 | 26.28 | 3.13 |
| 6 | 5 – 10 μ | Activation under cooling and hydrazine treatment | 67.45 | 23.05 | 2.24 |
| 7 | 0 – 5 μ | Activation under cooling | 62.90 | 23.63 | 2.91 |
| 8 | 0 – 5 μ | Activation under cooling and hydrazine treatment | 67.80 | 22.28 | 2.05 |

EXAMPLES 9 to 20

The following examples further illustrate typical electrodes of Raney-nickel amalgam of the invention and various conditions for their manufacture. Various Raney-alloys commercially available are used.

| Ex. | Grain Size | Amalgam Solution | Hg percent | Ni percent | Al percent |
|---|---|---|---|---|---|
| 9 | <40 μ | Hg (NO$_3$)$_2$ | 25.04 | 55.45 | 1.85 |
| 10 | <40 μ | '' | 10.35 | 67.27 | 2.31 |
| 11 | <40 μ | '' | 21.44 | 59.21 | 1.89 |
| 12 | 10–20 μ | '' | 41.32 | 38.43 | 2.76 |
| 13 | <40 μ | HgCl$_2$ | 47.18 | 36.21 | 8.20 |
| 14 | <40 μ | '' | 60.48 | 27.14 | 3.95 |
| 15 | 5–10 μ | '' | 61.78 | 26.28 | 3.13 |
| 16 | <100 μ | '' | 54.48 | 32.44 | 3.42 |
| 17 | 0–5 μ | '' | 62.90 | 25.63 | 2.91 |
| 18 | 0–5 μ | '' | 67.80 | 22.28 | 2.05 |
| 19 | 5–10 μ | '' | 67.45 | 23.05 | 2.24 |
| 20 | <40 μ | '' | 37.43 | 42.45 | 1.57 |

Activation in examples 9, 11–17 cold activation was carried (at temperatures not over 30°C); in example 10 it was 114°C; in examples 18 and 19, activation was also performed at about 15° to 22°C, but treatment with hydrazine preceded the amalgam formation; in example 20 the reactivation of deactivated Raney nickel was carried out at 20°C. and hydrazine was used too.

EXAMPLE 21

100 g Raney-iron-alloy (50 per cent by weight iron, 50 per cent by weight aluminum; grain size smaller than 40 $\mu$) is introduced slowly with strong cooling into 2 liter of 6 N NaOH, containing complex formers for the $Al_3^+$-ion. Hydrogen development upon dissolving out of the inactive component is terminated after approximately 3 to 4 hours.

As described in Example 1, 8 liters of an acidified, aqueous solution of 272 g of $HgCl_2$ are introduced into the above solution, containing Raney-iron. The mercury is rapidly taken up. The amalgamated iron is non-pyrophoric after washing with water and acetone.

The Raney-iron amalgam contains about 80 percent by weight of mercury.

Raney-iron takes on such a large volume of hydrogen during its activation that there can also be used $Hg(NO_3)_2$ for the amalgamation quite satisfactorily although a part of the active hydrogen is used up by the reduction of the nitrate ion to ammonia.

1.8 g of the iron amalgam is mixed with 0.2 g of graphite and pressed into an electrode between two fine screens of expanded nickel metal. The electrode has a content of 22.0 per cent by weight of iron and 62.7 per cent by weight of mercury.

Figure 4:
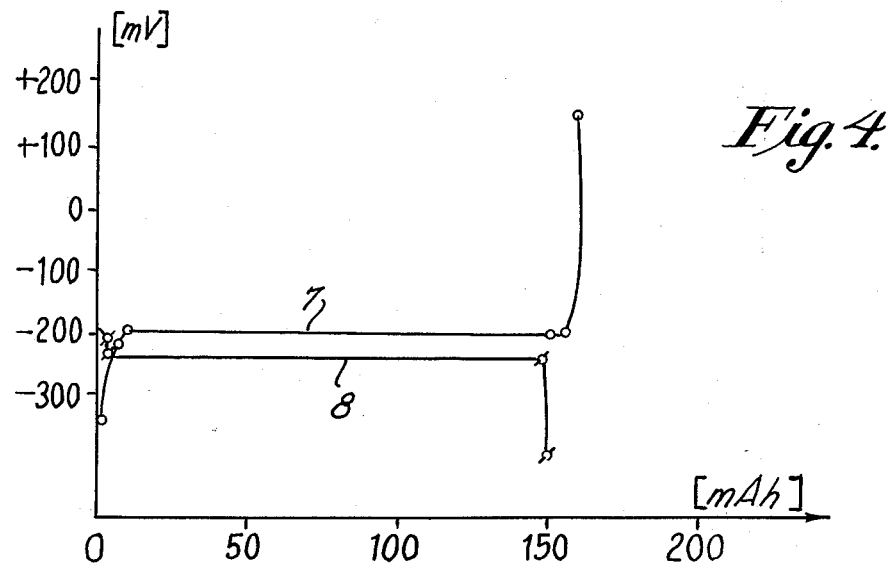
FIGS. 4 and 5 show charge and discharge curves of a particular electrode and a metal/oxygen element.

FIG. 4 shows the electrochemical measurement values. The individual potentials have been determined against a saturated calomel electrode. The charge curve 7 and the discharge curve 8 are shown. Charges and discharges were undertaken in each case with 10 mA/cm$^2$. As the electrode is tested through repeated cycles, it becomes apparent that the iron analgam electrode is particularly well suited as an electrode for primary cells. Pure iron amalgam particularly with a high Hg-content is less capable of tightly binding the mercury after repeated charging and discharging. The alloy Raney-iron-nickel, with increasing proportion of nickel reduces this property, which is undesirable for secondary cells.

EXAMPLE 22

100 g Raney-nickel-alloy is loaded with hydrogen as described in Example 1. Upon termination of the hydrogen development, 10 ml of 80% hydrazine hydrate solution are added to 2 liter of the solution with agitation. After 3 to 4 minutes hydrogen development begins, ending after 25 to 40 minutes. This additional treatment with a reducing agent causes a considerably faster sorbtion of the Hg at the subsequent amalgamation and, simultaneously, it causes a significant increase of the sorption power of the Raney-nickel for Hg. However, for best results it is desirable that all of the hydrazine be decomposed before amalgamation for suppressing the reduction of $Hg^{2+}$-ions to metallic mercury in the amalgamation solution and not on and by the matrix material.

In accordance with this improved process there is obtained an increase in the Hg content to more than 67 per cent by weight. Yet Raney-nickel with such high Hg-content shows hardly higher nickel oxides or nickel hydroxides potential levels in charging and discharging, very rapidly establishing the HgO/Hg potential and constant discharge rates.

EXAMPLE 23

1.5 g of polyisobutylene powder is allowed to stand over night in 150 cm$^3$ cyclohexane and, thereafter, 100 g of amalgamated Raney-nickel and 10 g graphite are added, following the procedures of Example 22. 11 g of sodium carbonate powder of particle diameter between 70 and 300 $\mu$ are added to preclude a swelling of the finished electrode. The mixture is homogenized, and the cyclohexane is evaporated in vacuo.

After drying, the material is formed through a fine screen and 5 g thereof is applied to each side of an expanded nickel metal insert and pressed into an electrode under pressure of 1000 kg/cm$^2$. Subsequently, the filler material is dissolved out with hot water. The operating surface of the electrode is 8 cm$^2$ The electrode is then connected in a mercury-zinc cell to a zinc electrode having a greater capacity. The distance between the electrodes is 20 mm. 6 N KOH is used as electrolyte (at 20°C) in which 50 g EnO/liter is dissolved.

Figure 5:
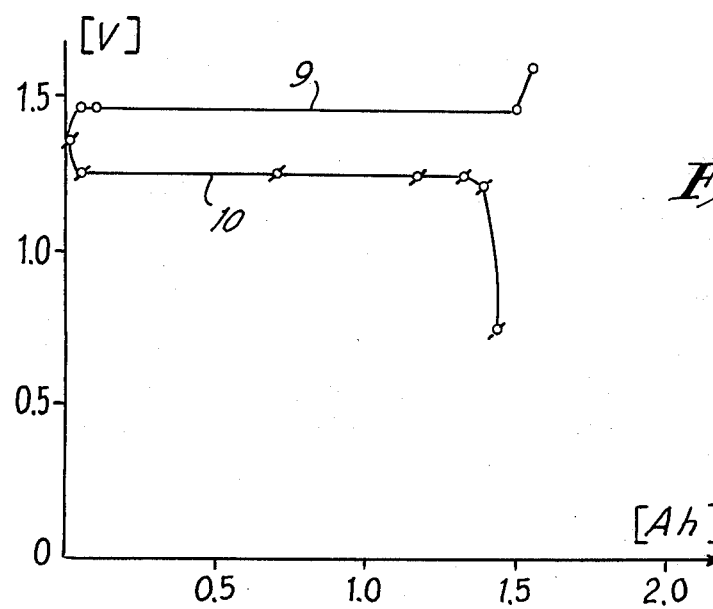

FIG. 5 shows the first charge curve 9 with 6 mA/cm$^2$, the first discharge curve 10 with 2 mA/cm$^2$. The charge- and discharge curves show a surprising consistency of their potential, with a steep break upon charge and discharge. The mercury electrode contains in addition to 20.85% Ni and 2.20% Al, 67.8% Hg; this high Hg-content prevents the occurrence of intermediate potentials normally caused by nickel is conventional electrodes. It is evident again that the cell of the invention rapidly reaches a potential which approximates the Hg/HgO potential, possesses a very regular, flat discharge curve and can be discharged of essentially all of their theoretical capacity.

Likewise, comparable results are obtained with an electrode of nickel-iron-cobalt (30-10-10% by weight) and mercury 50% by weight.

The electrode of this invention is used in batteries (dry cell, sealed storage and the like) and in primary cells thereof electrically connected to each other. The cell comprises the known elements and means like a metal anode, an alkaline aqueous salt electrolyte, and the reducible oxide cathode of the invention, preferably mixed with some form of carbon or metal for increased conductivity. Suitable separator means are used to prevent direct contact between the anode and cathode. See for instance, the article on *Batteries and Dry Cells* in the Encyclopedia, above cited, pages 70 – 95, including the references cited therein, which are incorporated herein by reference.

EXAMPLES 24 to 29

The performance of a cell of the invention using an electrode of the above-described alloys is further illustrated below.

An electrode of a pressed pellet (25.7 mm of diameter by 1.6–1.8 mm) of an alloy Raney-nickel-mercury containing 67.35% of mercury and 20% of graphite by weight is built into and connected in a cell (working surface 1 cm$^2$) connected to a nickel plate counter electrode. The cell has a theoretical capacity of 287.9 mAh. It is loaded with 350mAh. The table below illustrates a summary of this results.

TABLE I

| Ex. | Charge Current Charged | Amount Charged (mAh) | Discharge Current | Discharge Amount (mAh) | Capacity % of theory 287.9 |
|---|---|---|---|---|---|
| 24 | 100 mA | 350 | 5 mA | 65 | — |
| 25 | 50 mA | 350 | 5 mA | 175 | 60.9 |
| 26 | 15 mA | 350 | 5 mA | 235 | 81.7 |
| 27 | 10 mA | 350 | 5 mA | 250 | 87 |
| 28 | 5 mA | 350 | 5 mA | 280 | 97.5 |
| 29 | 3 mA | 350 | 5 mA | 280 | 97.5 |

When experiments 28 and 29 were repeated with a load of only 300 mAh, the amount discharged was still 200 mAh. It is apparent from the results that current discharge and the capacity of the cell are especially high at moderate and low current charges.

Also at low currents the amount of current that can be charged in the vicinity of the Hg/HgO potential is higher, as is shown below

| Charge Current | Amount charged at the Hg/HgO potential |
|---|---|
| 10 | 70 |
| 5 | 122.5 |
| 3 | 122.5 |

It is noteworthy too that the electrode of the invention assumes the Hg/HgO potential, (after about 3 hours when the current is disconnected) and after an assuming an initial over-potential.

To be noted too is that electrodes of alloy of Raney-nickel and mercury which have a graphite content of about 15 to 20% exhibit a sharper discharge curve at the end of the discharge and a higher total capacity.

Another application of the electrode of the invention is its use in alkaline zinc air cells. The Raney-nickel mercury electrode (8.5 g of 10 parts of Raney-nickel amalgam and 1 part of graphite) is connected in an assemby to a zinc counter-electrode in a SN KOH electrolyte.

The cell was operated for several months with oxygen gas. After having once charged the mercury electrode (capacity 1,2 Ah) with 60 mA, it could be discharged surprisingly with a constant current of 40 mA for over 8000 hours (320 Ab). The zinc electrode and the electrolyte were renewed if necessary.

The electrode after it had been allowed to break down could be made to recover readily be refeeding oxygen to it, after interruption of the oxygen when all of the cell's capacity had been discharged.

Similar rapid recovery with oxygen was obtained after the electrode was made to break down after feeding nitrogen to it.

The mercury Raney nickel, Raney iron and Raney cobalt alloys of the invention are also well suited for use as control or measuring electrodes. They possess a number of unexpected advantages over conventional electrodes such as mercury/mercury oxide electrode. They are readily cleaned and regenerated, a property which is especially important when the electrode is to be used sequentially in various liquids at different pH values. Also the electrode can be used in direct contact with the electrolyte, without glass components, thereby avoiding diffusion paths which effect readings.

When measurements are taken at pH values between 10 and 13 in a buffered solution at 25°C, the values obtained all are in a practical readable range. Alkaline concentrations are also readily measured with the measuring electrode. For the range of 0.1 to 6 molar alkali concentration the range is from 95 mV to 202 mV measured against a saturated calomel reference electrode.

The conventional mercury/mercury oxide electrodes do not contain an electrically conductive material. Hence they do not reach a rapid equilibrium between mercury and mercury oxide when the electrode is loaded. When a conventional electrode is compared with an Hg/HgO electrode of the invention, the first electrode shows a potential decrease of 60 mV after 3 months whereas the second electrode shows a potential decrease of 2 mV; measured against a saturated calomel electrode. In the meantime, the conventional electrode had blackened completely.

The alloy of the invention and electrodes made therefrom are especially useful for use at a temperature below about 80°C.

It is apparent from the above description that the electrodes of the invention exhibit a number of advantageous properties: they have a high capacity and are readily rechargeable. A very desirable characteristic of the cell is its relatively flat and constant discharge curve, with a current discharge approaching the theoretical capacity of the electrode.

I claim:

1. A rechargeable electrode having high capacity especially for primary cells and accumulators, which comprises a porous metal matrix having amalgamated thereon a non-pyrophoric amalgam of said matrix metal as non-migratory, non-coalescible, solid particles in fine state of physical distribution, said matrix being inert to alkali and being capable of absorbing hydrogen and the electrode being capable of repeated charging and discharging cycles during which the mercury is present as mercury oxide and mercury, respectively, but in either case without coalescing into mercury droplets, said electrode being capable of a flat and constant discharge curve, with a current discharge approaching the theoretical capacity of the electrode and said matrix being a Raney-metal of one of the following: Raney-nickel, Raney-iron, Raney-cobalt or alloys of these Raney metals.

2. The electrode of claim 1 wherein the matrix is Raney-nickel.

3. The electrode of claim 1 which has a mercury content of about 20 to about 70 percent by weight.

4. The electrode of claim 1 wherein the mercury oxide content is of about 20 to about 70 percent by weight.

5. The electrode of claim 1 wherein the electrode is of mercury oxide, in the charged state.

6. The electrode of claim 5 wherein the mercury oxide is taken up within the porous matrix and forms a coating on its surface.

7. The electrode of claim 2 comprising an electrically conductive material, in intimate mixture therewith.

8. The electrode of claims 7 comprising graphite.

9. The electrode of claim 2 wherein the matrix is nickel flakes.

10. The electrode of claim 1 wherein the amalgam has a mercury content of 50 to 80 percent by weight.

11. The electrode of claim 4 further comprising graphite in the amount of about 15 to 20 percent by weight, and which exhibits a sharp discharge curve at the end of the discharge period.

12. The electrode of claim 7 wherein the material is a metal, and the electrode is capable of reaching a rapid equilibrium upon loading.

13. The electrode of claim 1 wherein the matrix is a non-noble metal.

14. A rechargeable electrode for battery cells, said electrode comprising:
a Raney-nickel matrix, and
finely-divided powder coating on said matrix, said coating being an amalgam of nickel and mercury, said mercury changing from mercury oxide to mercury during discharging and from mercury to mercury oxide during charging, said matrix and coating being devoid of noble metal, and
said coating having been produced by steps which include
charging the nickel with hydrogen,
contacting said hydrogen-charged nickel with a mercury salt solution, and
maintaining said contact until the resultant electrode has a mercury content of about 50 to about 80 percent by weight.

15. The electrode of claim 14, wherein said contacting solution is an aqueous solution of mercuric chloride with hydrochloric acid, and said contact is maintained until said solution assumes a weak yellow coloration.

16. The electrode of claim 15, wherein said Raney nickel is in the form of a filter cake at the beginning of said solution contacting step, and further including the step of washing and drying said filter cake after said solution contacting step.

17. A rechargeable electrode having high capacity especially for primary cells and accumulators, which comprises a porous metal matrix having amalgamated thereon a non-pyrophoric amalgam of said matrix metal as non-migratory, non-coalescible, solid particles in fine state of physical distribution, said matrix being inert to alkali and being capable of absorbing hydrogen and the electrode being capable of repeated charging and discharging cycles during which the mercury is present as mercury oxide and mercury, respectively, but in either case without coalescing into mercury droplets, said electrode being capable of a flat and constant discharge curve, with a current discharge approaching the theoretical capacity of the electrode and said matrix being a Raney-metal of one of the following; Raney-nickel, Raney-iron, Raney-cobalt or alloys of these Raney metals, said electrode being made by a process which includes the steps of
charging the metal with hydrogen,
contacting said hydrogen-charged metal with a solution of mercury salt, whereby an amalgam of said metal is formed, and
maintaining said contact until the resultant electrode has a mercury content of about 50 to about 80 percent by weight.

* * * * *

UNITED STATES PATENT OFFICE
CERTIFICATE OF CORRECTION

Patent No. 3,966,493          Dated June 29, 1976

Inventor(s) Margarete Jung

It is certified that error appears in the above-identified patent and that said Letters Patent are hereby corrected as shown below:

On the Title Page:

Amend, in the second line, the name of the inventor "Jüng" to read ---Jung---.

Amend, in the line containing item [75], the name of the inventor, "Margarete Jüng" to read ---Margarete Jung ---.

Delete, the line containing the name of the assignee "[73] Assignee: Varta Batterie Aktiengesellschaft".

Signed and Sealed this

Seventh Day of December 1976

[SEAL]

Attest:

RUTH C. MASON
*Attesting Officer*

C. MARSHALL DANN
*Commissioner of Patents and Trademarks*